United States Patent
Suzuki

(10) Patent No.: US 11,365,280 B2
(45) Date of Patent: Jun. 21, 2022

(54) PHOTOCURABLE RESIN COMPOSITION

(71) Applicant: KURARAY NORITAKE DENTAL INC., Kurashiki (JP)

(72) Inventor: Kenji Suzuki, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 0 days.

(21) Appl. No.: 17/041,600

(22) PCT Filed: Mar. 28, 2019

(86) PCT No.: PCT/JP2019/013581
§ 371 (c)(1),
(2) Date: Sep. 25, 2020

(87) PCT Pub. No.: WO2019/189566
PCT Pub. Date: Oct. 3, 2019

(65) Prior Publication Data
US 2021/0024682 A1 Jan. 28, 2021

(30) Foreign Application Priority Data
Mar. 28, 2018 (JP) .............................. JP2018-063004

(51) Int. Cl.
| | | |
|---|---|---|
| C08F 2/46 | (2006.01) | |
| C08F 2/50 | (2006.01) | |
| C08G 61/04 | (2006.01) | |
| C08G 18/67 | (2006.01) | |
| B33Y 70/00 | (2020.01) | |
| B33Y 80/00 | (2015.01) | |
| B29C 64/314 | (2017.01) | |
| B33Y 40/10 | (2020.01) | |
| A61K 6/893 | (2020.01) | |
| C08F 290/06 | (2006.01) | |
| B33Y 10/00 | (2015.01) | |
| B29C 64/124 | (2017.01) | |
| B29K 33/00 | (2006.01) | |
| B29L 31/00 | (2006.01) | |

(52) U.S. Cl.
CPC .......... *C08G 18/6755* (2013.01); *A61K 6/893* (2020.01); *B29C 64/314* (2017.08); *B33Y 40/10* (2020.01); *B33Y 70/00* (2014.12); *B33Y 80/00* (2014.12); *C08F 290/061* (2013.01); *B29C 64/124* (2017.08); *B29K 2033/08* (2013.01); *B29L 2031/753* (2013.01); *B29L 2031/7536* (2013.01); *B33Y 10/00* (2014.12)

(58) Field of Classification Search
CPC ......... B33Y 70/00; B33Y 40/10; B33Y 80/00; B33Y 10/00; B29C 64/314; B29C 64/124; A61K 6/893; B29K 2033/08; C08G 18/6208; C08G 18/4238; C08G 18/44; C08G 18/672; C08G 18/246; C08G 18/755; C08G 18/6755; C08F 290/061; C08F 290/067; C08F 220/067; C08L 75/16; B29L 2031/7536; B29L 2031/753
USPC ............. 522/28, 7, 6, 71, 189, 184, 1; 520/1
See application file for complete search history.

(56) References Cited

U.S. PATENT DOCUMENTS

| | | | |
|---|---|---|---|
| 6,231,337 B1 | 5/2001 | Boyd | |
| 2009/0065140 A1* | 3/2009 | Osoegawa | ............. C09J 175/16 156/275.5 |
| 2015/0218405 A1* | 8/2015 | Iwata | ................. C09D 133/066 428/423.1 |
| 2016/0362567 A1 | 12/2016 | Ono et al. | |
| 2017/0009001 A1* | 1/2017 | Takenouchi | ......... C08G 18/672 |
| 2018/0244831 A1* | 8/2018 | Hirata | ................ C08G 18/6216 |
| 2018/0282455 A1 | 10/2018 | Sakamaki et al. | |

FOREIGN PATENT DOCUMENTS

| | | | |
|---|---|---|---|
| JP | 2000-159621 A | | 6/2000 |
| JP | 2006-28499 A | | 2/2006 |
| JP | 2006028499 | * | 2/2006 |

(Continued)

OTHER PUBLICATIONS

Hagiwara et al, JP 2006-028499 Machine Translation, Feb. 2, 2006 (Year: 2006).*

(Continued)

*Primary Examiner* — Jessica Whiteley
(74) *Attorney, Agent, or Firm* — Oblon, McClelland, Maier & Neustadt, L.L.P.

(57) ABSTRACT

The present invention provides a photocurable resin composition that has good fabricability, and that exhibits superior flexibility, fracture resistance, and water resistance in the form of a cured product. The present invention relates to a photocurable resin composition comprising:
  a urethanized (meth)acrylic compound (A);
  a mono(meth)acrylic acid ester compound (B) containing no urethane bond; and
  a photopolymerization initiator (C),
  the urethanized (meth)acrylic compound (A) being a (meth)acrylate comprising, per molecule, at least one kind of structure selected from the group consisting of a polyester, a polycarbonate, a polyurethane, a polyether, a poly-conjugated diene, and a hydrogenated poly-conjugated diene; and a urethane bond,
  the mono(meth)acrylic acid ester compound (B) containing no urethane bond comprising at least one selected from the group consisting of a mono(meth)acrylic acid ester compound (b-I) represented by general formula (I), and a mono(meth)acrylic acid ester compound (b-II) represented by general formula (II).

20 Claims, No Drawings

(56) References Cited

FOREIGN PATENT DOCUMENTS

| | | |
|---|---|---|
| JP | 2017-128688 A | 7/2017 |
| JP | 2017-179092 A | 10/2017 |
| JP | 2018-9102 A | 1/2018 |
| WO | WO 2006/118078 A1 | 11/2006 |
| WO | WO 2010/113600 A1 | 10/2010 |
| WO | WO-2010113600 A1 * 10/2010 ........... C07C 219/08 |
| WO | WO 2012/141275 A1 | 10/2012 |
| WO | WO-2012141275 A1 * 10/2012 .............. B32B 7/12 |
| WO | WO 2015/080142 A1 | 6/2015 |
| WO | WO 2015/141537 A1 | 9/2015 |
| WO | WO 2017/047615 A1 | 3/2017 |
| WO | WO 2017/061446 A1 | 4/2017 |

OTHER PUBLICATIONS

Kondou et al, WO 2010113600 Machine Translation, Oct. 7, 2010 (Year: 2010).*
Oikawa et al, WO 2012141275 Machine Translation, Oct. 18, 2012 (Year: 2012).*
International Search Report dated Jul. 2, 2019 in PCT/JP2019/013581 filed Mar. 28, 2019, 2 pages.
Extended European Search Report dated Dec. 2. 2021 in European Patent Application No. 197760119, 7 pages.

* cited by examiner

PHOTOCURABLE RESIN COMPOSITION

TECHNICAL FIELD

The present invention relates to a photocurable resin composition for use particularly in stereolithography, and to mouthguards, occlusal splints, and denture base materials comprising a cured product of the photocurable resin composition.

BACKGROUND ART

A mouthguard is a device worn in the mouth to protect the stomatognathic system and the brain by reducing injuries caused when large external forces are applied to teeth and jawbones during sports activities, notably in contact sports such as karate, boxing, American football, rugby, and soccer. The active promotion of sports participation in recent years has led to making wearing of a mouthguard compulsory in contact sports, and it has become increasing common to recommend the use of a mouthguard in other sports as well. The same trend is seen in the environment of education, where school children are recommended to wear a mouthguard for the prevention of possible mouth injuries during sports activities such as in physical education classes.

An occlusal splint, similar in form to a mouthguard, is an appliance that is worn while sleeping to prevent tooth wear due to clenching, or to straighten teeth.

A denture base material is a material that simulates the gum for the placement of a denture replacing missing teeth. Over the last years, the demand for dentures has rapidly increased with population aging.

Flexibility, shock absorption, fracture resistance (the property of a material to resist the development of a fracture), and water resistance are common requirements for mouthguards, occlusal splints, and denture base materials. A loss of flexibility leads to discomfort, whereas a loss of shock absorption results in the impact of external and occlusal forces being directly transmitted to the jawbones. Making these appliances less resistant to fracture is also problematic because it necessitates frequent replacement. When water resistance is no longer maintained, the appliances become cosmetically unappealing as a result of clouding of color, and fails to provide a good texture against the tongue and lips, in addition to posing a risk of possible fracture while in use.

Another consideration is that fabrication of a mouthguard, an occlusal splint, and a denture base material typically requires taking an impression of the oral cavity. However, the procedure involves discomfort, and places a burden on patients, in addition to requiring high technical skills. Recent advances in digital technology has led to approaches that make use of an intraoral optical scan for taking an oral impression, and there have been attempts to apply stereolithography techniques for the formation of dental appliances such as above. To this end, photocurable resin compositions are used. As a rule, resin compositions that develop flexibility and water resistance are usually high in low-polarity monomers and low in curability, and cured products of such resin compositions tend to have poor mechanical strength. Indeed, it has been difficult to satisfy mechanical strength, flexibility, and water resistance at the same time, particularly in stereolithography, where notably short photoirradiation times are employed. Resin compositions are also required to have a viscosity sufficient to enable fabrication. However, many of the monomers that develop mechanical strength have high viscosity, and reducing the viscosity of such monomers remains difficult.

Against this backdrop, various techniques are proposed that enable stereolithographic production of a cured product having desirable flexibility and desirable mechanical strength. For example, Patent Literature 1 proposes a photocurable resin composition comprising a urethane-base oligomer. Patent Literature 2 proposes a photocurable resin composition having desirable toughness that can be used as material of mouthpieces, denture bases, and artificial teeth. A technique for achieving low viscosity without impairing the curability of a photocurable resin composition is also available, as disclosed in Patent Literatures 3 to 5, which propose photocurable resin compositions for use in optical materials and achieving low viscosity by addition of a monofunctional monomer having an aromatic ring.

CITATION LIST

Patent Literature

Patent Literature 1: JP 2006-28499 A
Patent Literature 2: WO 2017/061446 A1
Patent Literature 3: WO 2015/080142 A1
Patent Literature 4: WO 2010/113600 A1
Patent Literature 5: JP 2017-128688 A

SUMMARY OF INVENTION

Technical Problem

Patent Literature 1 does not describe anything about water resistance of the photocurable resin composition. The photocurable resin composition described in Patent Literature 2 has high elastic modulus, and the flexibility is insufficient. This related art also does not describe anything about water resistance. The photocurable resin compositions described in Patent Literatures 3 and 4 are intended for hard materials, and there is no description about flexibility. Patent Literature 5 is also silent as to water resistance, though the descriptions discuss the flexibility of the photocurable resin composition.

It is accordingly an object of the present invention to provide a photocurable resin composition that is low in viscosity and has good fabricability, and that exhibits superior flexibility, shock absorption, fracture resistance, and water resistance in the form of a cured product, and, particularly, a photocurable resin composition suited for mouthguards, occlusal splints, and denture base materials formed by stereolithography. Another object of the present invention is to provide a mouthguard, an occlusal splint, and a denture base material comprising a cured product of the photocurable resin composition.

Solution to Problem

Specifically, the present invention provides the following.
[1] A photocurable resin composition comprising:
  a urethanized (meth)acrylic compound (A);
  a mono(meth)acrylic acid ester compound (B) containing no urethane bond; and
  a photopolymerization initiator (C),
  the urethanized (meth)acrylic compound (A) being a (meth)acrylate comprising, per molecule, at least one kind of structure selected from the group consisting of a polyester, a polycarbonate, a polyurethane, a polyether, a poly-conjugated diene, and a hydrogenated poly-conjugated diene; and a urethane bond, the mono(meth)acrylic acid ester compound (B) containing no urethane bond comprising at least one selected from the group consisting of a mono(meth)acrylic acid ester compound (b-I) represented by the following general formula (I), and a mono(meth)acrylic acid ester compound (b-II) represented by the following general formula (II),

[Chem. 1]

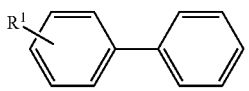
(I)

[Chem. 2]

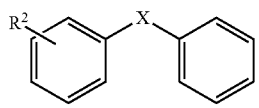
(II)

where $R^1$ and $R^2$ each independently represent a group represented by the following general formula (i) or a group represented by the following general formula (ii), and X is a divalent hydrocarbon group having 1 to 6 carbon atoms, or an oxygen atom,

[Chem. 3]

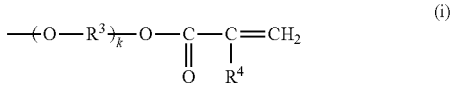
(i)

[Chem. 4]

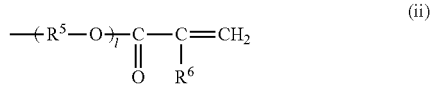
(ii)

where $R^3$ and $R^5$ each independently represent a divalent hydrocarbon group having 1 to 10 carbon atoms, $R^4$ and $R^6$ each independently represent a hydrogen atom or a methyl group, and k and l are each independently an integer of 0 to 6.

[2] The photocurable resin composition of [1], further comprising a (meth)acrylamide compound (D).
[3] The photocurable resin composition of [1] or [2], wherein $R^4$ and $R^6$ are hydrogen atoms.
[4] The photocurable resin composition of any one of [1] to [3], wherein k and l are 0 or 1.
[5] The photocurable resin composition of any one of [1] to [4], wherein the mono(meth)acrylic acid ester compound (B) containing no urethane bond comprises the mono(meth)acrylic acid ester compound (b-II), and X is an oxygen atom.
[6] The photocurable resin composition of [5], wherein $R^2$ is a group represented by the general formula (ii).
[7] The photocurable resin composition of any one of [1] to [6], wherein the mono(meth)acrylic acid ester compound (B) containing no urethane bond comprises the mono(meth)acrylic acid ester compound (b-I), and $R^1$ is a group represented by the general formula (i).
[8] The photocurable resin composition of any one of [1] to [7], wherein the photocurable resin composition is for stereolithography.
[9] A mouthguard comprising a cured product of the photocurable resin composition of any one of [1] to [8].
[10] An occlusal splint comprising a cured product of the photocurable resin composition of any one of [1] to [8].
[11] A denture base material comprising a cured product of the photocurable resin composition of any one of [1] to [8].
[12] A method for stereolithographically producing a three-dimensional object with the photocurable resin composition of any one of [1] to [8].

Advantageous Effects of Invention

A photocurable resin composition of the present invention is low in viscosity and has good fabricability, and exhibits superior flexibility, shock absorption, fracture resistance, and water resistance in the form of a cured product. This makes a photocurable resin composition of the present invention particularly suited for mouthguards and occlusal splints formed by stereolithography, and preferred for use also as a denture base material.

DESCRIPTION OF EMBODIMENTS

A photocurable resin composition of the present invention comprises a urethanized (meth)acrylic compound (A), a mono(meth)acrylic acid ester compound (B) containing no urethane bond, and a photopolymerization initiator (C). The urethanized (meth)acrylic compound (A) is a (meth)acrylate comprising, per molecule, at least one kind of structure selected from the group consisting of a polyester, a polycarbonate, a polyurethane, a polyether, a poly-conjugated diene, and a hydrogenated poly-conjugated diene (hereinafter, these will be referred to also as "polymer backbones"); and a urethane bond. The mono(meth)acrylic acid ester compound (B) containing no urethane bond comprises at least one selected from the group consisting of a mono (meth)acrylic acid ester compound (b-I) represented by the foregoing general formula (I), and a mono(meth)acrylic acid ester compound (b-II) represented by the foregoing general formula (II). In the present specification, the upper limits and lower limits of numeric ranges (for example, ranges of contents of components, ranges of values calculated from components, ranges of values of physical properties) can be combined appropriately. In the present specification, the numeric values represented by symbols in various formulae also can be combined as appropriate.

Urethanized (Meth)Acrylic Compound (A)

In a photocurable resin composition of the present invention, the urethanized (meth)acrylic compound (A) is used to impart water resistance, shock absorption, and strength to a cured product of the photocurable resin composition.

The urethanized (meth)acrylic compound (A) can be synthesized with ease through, for example, an addition reaction of a polyol containing the polymer backbone, a compound having an isocyanate group (—NCO), and a (meth)acrylate compound having a hydroxyl group (—OH). The urethanized (meth)acrylic compound (A) also can be synthesized with ease through a ring-opening addition reaction whereby a (meth)acrylate compound having a hydroxyl group is reacted upon by lactone or alkylene oxide, and the resulting compound having a hydroxyl group at one end is subjected to an addition reaction with a compound having an isocyanate group.

The urethanized (meth)acrylic compound (A) comprises a structure selected from the group consisting of a polyester, a polycarbonate, a polyurethane, a polyether, a poly-conjugated diene, and a hydrogenated poly-conjugated diene. These are not limited to particular types of compounds, as long as the urethanized (meth)acrylic compound (A) comprises a structure selected from these. Examples of the polyester include a polymer of phthalic acid and an alkylenediol having 2 to 12 carbon atoms, a polymer of adipic acid and an alkylene glycol having 2 to 12 carbon atoms, a polymer of maleic acid and an alkylenediyl having 2 to 12 carbon atoms, a β-propiolactone polymer, a γ-butyrolactone polymer, a δ-valerolactone polymer, an r-caprolactone polymer, and copolymers of these. Examples of the polycarbonate include a polycarbonate derived from an aliphatic diol having 2 to 12 carbon atoms, a polycarbonate derived from bisphenol A, and a polycarbonate derived from a C2 to C12 aliphatic diol and bisphenol A. Examples of the polyurethane include a polymer of a C2 to C12 aliphatic diol and a C1 to C12 diisocyanate. Examples of the polyether include polyethylene glycol, polypropylene glycol, polybutylene glycol, and poly(1-methylbutyleneglycol). Examples of the poly-conjugated diene and the hydrogenated poly-conjugated diene include 1,4-polybutadiene, 1,2-polybutadiene, polyisoprene, poly(butadiene-isoprene), poly(butadiene-styrene), poly(isoprene-styrene), poly-farnesene, and hydrogenated products of these. In view of desirable strength and water resistance, the preferred structures are polyesters, polycarbonates, and poly-conjugated dienes. A polyol having the polymer backbone can be used for the production of the urethanized (meth)acrylic compound (A).

Examples of the compound having an isocyanate group include hexamethylene diisocyanate (HDI), tolylene diisocyanate (TDI), xylylene diisocyanate (XDI), diphenylmethane diisocyanate (MDI), isophorone diisocyanate trimethylhexamethylene diisocyanate (TMHMDI), tricyclodecane diisocyanate (TCDDI), and adamantane diisocyanate (ADI).

Examples of the (meth)acrylate compound having a hydroxyl group include hydroxy(meth)acrylate compounds such as 2-hydroxyethyl(meth)acrylate, 2-hydroxypropyl(meth)acrylate, 2-hydroxybutyl(meth)acrylate, 6-hydroxyhexyl(meth)acrylate, 10-hydroxydecyl(meth)acrylate, 3-chloro-2-hydroxypropyl(meth)acrylate, 2-hydroxy-3-phenoxypropyl(meth)acrylate, glycerin mono(meth)acrylate, N-hydroxyethyl(meth)acrylamide, N,N-bis(2-hydroxyethyl) (meth)acrylamide, 2-hydroxy-3-acryloyloxypropyl(meth) acrylate, 2,2-bis[4-[3-(meth)acryloyloxy-2-hydroxypropoxy]phenyl]propane, 1,2-bis[3-(meth)acryloyloxy-2-hydroxypropoxy]ethane, pentaerythritol tri(meth)acrylate, and tri or tetra(meth)acrylate of dipentaerythritol.

The addition reaction between a compound having an isocyanate group and a (meth)acrylate compound having a hydroxyl group may follow a known method, and is not particularly limited.

The urethanized (meth)acrylic compound (A) obtained may be a reaction product of any combination of a polyol having at least one kind of structure selected from the group consisting of a polyester, a polycarbonate, a polyurethane, a polyether, a poly-conjugated diene, and a hydrogenated poly-conjugated diene; a compound having an isocyanate group; and a (meth)acrylate compound having a hydroxyl group.

A feature of the urethanized (meth)acrylic compound (A) is that it comprises the polymer backbone and an urethane bond. The urethanized (meth)acrylic compound (A) may be one synthesized by, for example, an addition reaction of a polyol having a structure derived from a C4 to C18 aliphatic chain diol unit (a) having a branched structure; a compound having an isocyanate group (—NCO); and a (meth)acrylate having a hydroxyl group (—OH). The urethanized (meth) acrylic compound (A) may be a compound in which a polyester polyol having a structure derived from a C4 to C18 aliphatic chain diol unit (a) having a branched structure, and other polyol (for example, a polyester polyol having a structure derived from a C4 to C18 aliphatic chain dicarboxylic acid and/or aromatic dicarboxylic acid unit (b) having no branched structure) coexist per molecule via a diisocyanate group.

As discussed above, it is important that the urethanized (meth)acrylic compound (A) comprise, per molecule, at least one kind of structure selected from the group consisting of a polyester, a polycarbonate, a polyurethane, a polyether, a poly-conjugated diene, and a hydrogenated poly-conjugated diene. Preferably, the urethanized (meth)acrylic compound (A) is a (meth)acrylate in which the aforementioned specific structure derived from a C4 to C18 aliphatic chain diol unit (a) having a branched structure is present as a polymer backbone per molecule. More preferably, the urethanized (meth)acrylic compound (A) is a (meth)acrylate comprising, per molecule, a polymer backbone that is at least one kind of structure selected from the group consisting of: a polyester having a structure derived from the aliphatic chain diol unit (a), and a structure derived from a C4 to C18 aliphatic chain dicarboxylic acid and/or aromatic dicarboxylic acid unit (b) having no branched structure; and a polycarbonate having a structure derived from the aliphatic chain diol unit (a), and a structure derived from a C4 to C18 aliphatic chain diol unit (c) having no branched structure. Examples of the polyester include a copolymer having a structure derived from a C4 to C18 aliphatic chain diol unit (a) having a branched structure, and a structure derived from a C4 to C18 aliphatic chain dicarboxylic acid and/or aromatic dicarboxylic acid unit (b) having no branched structure. Examples of the polycarbonate include a copolymer having a structure derived from a C4 to C18 aliphatic chain Diol unit (a) having a branched structure, and a structure derived from a C4 to C18 aliphatic chain diol unit (c) having no branched structure. Examples of the polyurethane include a polycondensate formed through a condensation reaction of a diisocyanate compound with a structure derived from a C4 to C18 aliphatic chain diol unit (a) having a branched structure. Examples of the polyether include a polyether having a structure derived from a C4 to C18 aliphatic chain diol unit (a) having a branched structure, and a polyether having a structure derived from a C4 to C18 aliphatic chain diol unit (c) having no branched structure. Examples of the poly-conjugated diene include homopolymers or copolymers of conjugated diene monomers. Examples of the conjugated diene monomers include 1,3-butadiene, isoprene, 2,3-dimethyl-1,3-butadiene, 1,3-pentadiene, and 1,3-hexadiene. Examples of the hydrogenated poly-conjugated diene include hydrogenated polybutadiene, hydrogenated polyisoprene, and hydrogenated polyisobutylene. In view of desirable toughness and water resistance, the urethanized (meth) acrylic compound (A) preferably comprises a polymer backbone that is at least one kind of structure selected from the group consisting of a polyester, a polycarbonate, a polyether, and a hydrogenated poly-conjugated diene, more preferably a polymer backbone that is at least one kind of structure selected from the group consisting of a polyester, a polycarbonate, and a polyether.

Examples of the C4 to C18 aliphatic chain diol unit (a) having a branched structure include 2-methyl-1,3-propanediol, 2,2-diethyl-1,3-propanediol, 1,3-butanediol, 2-methyl-1,4-butanediol, neopentyl glycol, 3-methyl-1,5-pentanediol, 2-methyl-1,8-octanediol, 2,7-dimethyl 1,8-octanediol, 2-methyl-1,9-nonanediol, 2,8-dimethyl-1,9-nonanediol, 2-methyl-1,10-decanediol, 2,9-dimethyl-1,10-decanediol, 2-methyl-1,11-undecanediol, 2,10-dimethyl-1,11-undecane 2-methyl-1,12-dodecanediol, 2,11-dimethyl-1,12-dodecanediol, 2-methyl-1,13-tridecanediol, 2,12-dimethyl-1,13-tridecanediol, 2-methyl-1,14-tetradecanediol, 2,13-dimethyl-1,14-tetradecanediol, 2-methyl-1,15-pentadecanediol, 2,14-dimethyl-1,15-pentadecanediol, 2-methyl-1,16-hexadecanediol, and 2,15-dimethyl-1,16-hexadecanediol. In view of improving the curability and lowering the viscosity of the photocurable resin composition, it is preferable that the polyol used be a C5 to C12 aliphatic diol having a methyl side chain, such as 2-methyl-1,4-butanediol, 3-methyl-1,5-pentanediol, 2-methyl-1,8-octanediol, 2,7-dimethyl-1,8-octanediol, 2-methyl-1,9-nonanediol, or 2,8-dimethyl-1,9-nonanediol. The polyol is more preferably 2-methyl-1,4-butanediol, 3-methyl-1,5-pentanediol, 2-methyl-1,8-octanediol, or 2,7-dimethyl-1,8-octanediol, even more preferably 3-methyl-1,5-pentanediol or 2-methyl-1,8-octanediol.

Examples of the C4 to C18 aliphatic chain dicarboxylic acid and/or aromatic dicarboxylic acid unit (b) having no branched structure include succinic acid, maleic acid, fumaric acid, glutaric acid, adipic acid, pimelic acid, suberic acid, azelaic acid, sebacic acid, dodecanedioic acid, undecanedioic acid, tridecanedioic acid, tetradecanedioic acid, pentadecanedioic acid, hexadecanedioic acid, phthalic acid, terephthalic acid, and isophthalic acid. In view of improving the curability of the photocurable resin composition and the water resistance of the cured product, the C4 to C18 aliphatic chain dicarboxylic acid and/or aromatic dicarboxylic acid unit (b) having no branched structure is preferably adipic acid, pimelic acid, suberic acid, azelaic acid, sebacic acid, terephthalic acid, or isophthalic acid, more preferably adipic acid, sebacic acid, or isophthalic acid.

Examples of the C4 to C18 aliphatic chain diol unit (c) having no branched structure include butanediol, pentanediol, hexanediol, heptanediol, octanediol, nonanediol, decanediol, dodecanediol, undecanediol, tridecanediol, tetradecanediol, pentadecanediol, hexadecanediol, heptadecanediol, and octadecanediol. In view of improving the curability of the photocurable resin composition and the water resistance of the cured product, the C4 to C18 aliphatic chain diol unit (c) having no branched structure is preferably hexanediol, octanediol, nonanediol, decanediol, dodecanediol, or undecanediol, more preferably hexanediol, octanediol, nonanediol, or decanediol, even more preferably hexanediol or nonanediol.

In view of viscosity and strength, the weight-average molecular weight (Mw) of urethanized (meth)acrylic compound (A) is preferably 500 to 50,000, more preferably 750 to 30,000, even more preferably 1,000 to 15,000. The urethanized (meth)acrylic compound (A) may be used alone, or two or more thereof may be used in combination.

The content of urethanized (meth)acrylic compound (A) in the photocurable resin composition of the present invention is preferably 10 to 99 mass % relative to the total amount of urethanized (meth)acrylic compound (A), mono(meth)acrylic acid ester compound (B) containing no urethane bond, and (meth)acrylamide compound (D). In view of further improving fabricability, and the flexibility, shock absorption, fracture resistance, and water resistance of the cured product, the content of urethanized (meth)acrylic compound (A) is more preferably 30 to 95 mass %, even more preferably 50 to 90 mass %.

Mono(Meth)Acrylic Acid Ester Compound (B) Containing no Urethane Bond

In a photocurable resin composition of the present invention, the mono(meth)acrylic acid ester compound (B) containing no urethane bond is a compound that can lower the viscosity of the photocurable resin composition, and is used to impart flexibility and water resistance to the cured product.

The mono(meth)acrylic acid ester compound (B) containing no urethane bond comprises at least one selected from the group consisting of a mono(meth)acrylic acid ester compound (b-I) represented by the foregoing general formula (I) (hereinafter referred to as "mono(meth)acrylic acid ester compound (b-I)"), and a mono(meth)acrylic acid ester compound (b-II) represented by the foregoing general formula (II) (hereinafter referred to as "mono(meth)acrylic acid ester compound (b-II)"). Preferably, the mono(meth)acrylic acid ester compound (B) containing no urethane bond is a mono(meth)acrylic acid ester compound containing an aromatic ring. The following describes the mono(meth)acrylic acid ester compound (b-I) and mono(meth)acrylic acid ester compound (b-II).

The symbols in formula (I) are described below. In formula (I), $R^1$ is a group represented by the foregoing general formula (i) or a group represented by the foregoing general formula (ii). In view of improving the curability of a photocurable resin composition of the present invention, $R^4$ and $R^6$ in formula (i) or (ii) each independently represent a hydrogen atom or a methyl group. In view of improving the curability of the photocurable resin composition and the flexibility of the cured product, $R^4$ and $R^6$ are preferably hydrogen atoms. $R^3$ and $R^5$ each independently represent a divalent hydrocarbon group having 1 to 10 carbon atoms. In view of lowering the viscosity and improving the curability of the photocurable resin composition, the hydrocarbon group has preferably 1 to 6 carbon atoms, more preferably 1 to 4 carbon atoms, even more preferably 1 to 3 carbon atoms. Examples of the hydrocarbon group include a linear or branched alkylene group having 1 to 10 carbon atoms; a divalent cycloalkylene group having 3 to 10 carbon atoms; and a phenylene group. The symbols k and l each independently represent an integer of 0 to 6. In view of lowering the viscosity and improving the curability of the photocurable resin composition, k is preferably 0 to 4, more preferably 0 to 3, even more preferably 0 to 2, particularly preferably 0 or 1. The symbol l is preferably 0 to 4, more preferably 0 to 2, even more preferably 0 or 1.

Examples of the mono(meth)acrylic acid ester compound (b-I) include o-phenylphenol(meth)acrylate, m-phenylphenol(meth)acrylate, p-phenylphenol(meth)acrylate, methoxylated-o-phenylphenol(meth)acrylate, methoxylated-m-phenylphenol(meth)acrylate, methoxylated-p-phenylphenol(meth)acrylate, ethoxylated-o-phenylphenonmeth)acrylate, ethoxylated-m-phenylphenol(meth)acrylate, ethoxylated-p-phenylphenol(meth)acrylate, propoxylated-o-phenylphenonmeth)acrylate, propoxylated-m-phenylphenol(meth)acrylate, propoxylated-p-phenylphenol(meth)acrylate, butoxylated-o-phenylphenol(meth)acrylate, butoxylated-m-phenylphenol(meth)acrylate, and butoxylated-p-phenylphenol(meth)acrylate. These may be used alone, or two or more thereof may be used in combination. In view of improving the curability of the photocurable resin composition and the flexibility and water resistance of the cured product, the mono(meth)acrylic acid ester compound (b-I) is more preferably ethoxylated-o-phenylphenol acrylate, ethoxylated-m-phenylphenol acrylate, ethoxylated-p-phenylphenol acrylate, propoxylated-o-phenylphenol acrylate, propoxylated-m-phenylphenol acrylate, or propoxylated-p-phenylphenol acrylate, even more preferably ethoxylated-o-phenylphenol acrylate, ethoxylated-m-phenylphenol acrylate, or ethoxylated-p-phenylphenol acrylate, particularly preferably ethoxylated-o-phenylphenol acrylate or ethoxylated-m-phenylphenol acrylate, most preferably ethoxylated-o-phenylphenol acrylate.

The symbols in formula (II) are described below. In formula (II), X is a divalent hydrocarbon group having 1 to 6 carbon atoms, or an oxygen atom. In view of lowering the viscosity and improving the curability of the photocurable resin composition, X is preferably an oxygen atom. $R^2$ is a group selected from the foregoing general formula (i) and (ii). In view of improving the curability of a photocurable resin composition of the present invention, $R^4$ and $R^6$ in formula (i) or (ii) each independently represent a hydrogen atom or a methyl group. In view of improving the curability of the photocurable resin composition and the flexibility of the cured product, $R^4$ and $R^6$ are preferably hydrogen atoms. $R^3$ and $R^5$ each independently represent a divalent hydrocarbon group having 1 to 10 carbon atoms. In view of lowering the viscosity and improving the curability of the photocurable resin composition, the hydrocarbon group preferably has 1 to 6 carbon atoms, more preferably 1 to 4 carbon atoms, even more preferably 1 to 3 carbon atoms. Examples of the hydrocarbon group include a linear or branched alkylene group having 1 to 10 carbon atoms; a divalent cycloalkylene group having 3 to 10 carbon atoms; and a phenylene group. The symbols k and l each independently represent an integer of 0 to 6. In view of lowering the viscosity and improving the curability of the photocurable resin composition, k is preferably 0 to 4, more preferably 0 to 3, even more preferably 0 to 2, yet more preferably 0 or 1. The symbol l is preferably 0 to 4, more preferably 0 to 2, even more preferably 0 or 1.

Examples of the mono(meth)acrylic acid ester compound (b-II) include o-phenoxybenzyl(meth)acrylate, m-phenoxybenzyl(meth)acrylate, p-phenoxybenzyl(meth)acrylate, 2-(o-phenoxyphenyl)ethyl(meth)acrylate, 2-(m-phenoxyphenyl)ethyl(meth)acrylate, 2-(p-phenoxyphenyl)ethyl (meth)acrylate, 3-(o-phenoxyphenyl)propyl(meth)acrylate, 3-(m-phenoxyphenyl)propyl(meth)acrylate, 3-(p-phenoxyphenyl)propyl(meth)acrylate, 4-(o-phenoxyphenyl)butyl (meth)acrylate, 4-(m-phenoxyphenyl)butyl(meth)acrylate, 4-(p-phenoxyphenyl)butyl(meth)acrylate, 5-(o-phenoxyphenyl)pentyl(meth)acrylate, 5-(m-phenoxyphenyl)pentyl (meth)acrylate, 5-(p-phenoxyphenyl)pentyl(meth)acrylate, 6-(o-phenoxyphenyl)hexyl(meth)acrylate, 6-(m-phenoxyphenyl)hexyl(meth)acrylate, and 6-(p-phenoxyphenyl)hexyl (meth)acrylate. These may be used alone, or two or more thereof may be used in combination. In view of improving the curability of the photocurable resin composition and the flexibility and water resistance of the cured product, the mono(meth)acrylic acid ester compound (b-II) is more preferably o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, or 2-(p-phenoxyphenyl)ethyl acrylate, even more preferably o-phenoxybenzyl acrylate, m-phenoxybenzyl acrylate, or p-phenoxybenzyl acrylate, particularly preferably o-phenoxybenzyl acrylate or m-phenoxybenzyl acrylate, most preferably m-phenoxybenzyl acrylate.

The content of mono(meth)acrylic acid ester compound (B) containing no urethane bond in the photocurable resin composition of the present invention is preferably 1.0 to 90 mass % relative to the total amount of urethanized (meth) acrylic compound (A), mono(meth)acrylic acid ester compound (B) containing no urethane bond, and (meth)acrylamide compound (D). In view of further improving fabricability, and the flexibility, shock absorption, fracture resistance, and water resistance of the cured product, the content of mono(meth)acrylic acid ester compound (B) containing no urethane bond is more preferably 5 to 80 mass %, even more preferably 10 to 70 mass %.

The polymerizable monomer contained in a photocurable resin composition of the present invention may consist essentially of urethanized (meth)acrylic compound (A) and mono(meth)acrylic acid ester compound (B) containing no urethane bond, or may consist essentially of urethanized (meth)acrylic compound (A), mono(meth)acrylic acid ester compound (B) containing no urethane bond, and (meth) acrylamide compound (D). A polymerizable monomer consisting essentially of urethanized (meth)acrylic compound (A) and mono(meth)acrylic acid ester compound (B) containing no urethane bond means that the content of polymerizable monomers other than the urethanized (meth)acrylic compound (A) and the mono(meth)acrylic acid ester compound (B) containing no urethane bond is less than 10.0 mass %, preferably less than 5.0 mass %, more preferably less than 1.0 mass %, even more preferably less than 0.1 mass %, particularly preferably less than 0.01 mass % of the total amount of the polymerizable monomers contained in the photocurable resin composition.

Photopolymerization Initiator (C)

The photopolymerization initiator (C) used in the present invention may be selected from common polymerization initiators used in industry, preferably from photopolymerization initiators used in dentistry.

Examples of the photopolymerization initiator (C) include (bis)acylphosphine oxides, thioxanthones or quaternary ammonium salts of thioxanthones, ketals, α-diketones, coumarins, anthraquinones, benzoin alkyl ether compounds, and α-aminoketone compounds. The photopolymerization initiator (C) may be used alone, or two or more thereof may be used in combination.

Preferably, the photopolymerization initiator (C) is at least one selected from the group consisting of (bis)acylphosphine oxides and α-diketones. In this way, a photocurable resin composition can be obtained that has desirable photocurability both in the ultraviolet and visible regions, and that shows sufficient photocurability regardless of whether the light source used is a laser, a halogen lamp, a light emitting diode (LED), or a xenon lamp.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Other examples include the compounds mentioned in JP 2000-159621 A.

Among these (bis)acylphosphine oxides, particularly preferred as photopolymerization initiator (C) are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Camphorquinone is particularly preferred when the light source used is a visible-light source.

The content of photopolymerization initiator (C) in the photocurable resin composition of the present invention is not particularly limited. However, in view of the curability and other properties of the photocurable resin composition obtained, the content of photopolymerization initiator (C) is preferably 0.01 to 20 parts by mass relative to total 100 parts by mass of urethanized (meth)acrylic compound (A), mono (meth)acrylic acid ester compound (B) containing no urethane bond, and (meth)acrylamide compound (D). With less than 0.01 parts by mass of photopolymerization initiator (C), polymerization may fail to sufficiently proceed, and it may not be possible to form the photocurable resin composition into a product. The content of photopolymerization initiator (C) is more preferably at least 0.05 parts by mass, even more preferably at least 0.1 parts by mass, particularly preferably at least 0.5 parts by mass relative to total 100 parts by mass of urethanized (meth)acrylic compound (A), mono(meth)acrylic acid ester compound (B) containing no urethane bond, and (meth)acrylamide compound (D). With more than 20 parts by mass of photopolymerization initiator (C), the photopolymerization initiator (C) may precipitate from the photocurable resin composition when the solubility of the photopolymerization initiator itself is low. The content of photopolymerization initiator (C) is more preferably at most 15 parts by mass, even more preferably at most 10 parts by mass, particularly preferably at most 5.0 parts by mass relative to total 100 parts by mass of urethanized (meth) acrylic compound (A), mono(meth)acrylic acid ester compound (B) containing no urethane bond, and (meth)acrylamide compound (D).

The photocurable resin composition of the present invention is not particularly limited, as long as it comprises the urethanized (meth)acrylic compound (A), the mono(meth) acrylic acid ester compound (B) containing no urethane bond, and the photopolymerization initiator (C). For example, the photocurable resin composition of the present invention may be a photocurable resin composition comprising other components, in addition to these components. The photocurable resin composition of the present invention may be produced following a known method.

(Meth)Acrylamide Compound (D)

Preferably, the photocurable resin composition of the present invention further comprises a (meth)acrylamide compound (D). The (meth)acrylamide compound (D) is not particularly limited, as long as it has a (meth)acrylamide backbone. Examples of the (meth)acrylamide compound (D) include monofunctional (meth)acrylamide compounds such as N,N-dimethyl(meth)acrylamide, N,N-diethyl(meth)acrylamide, N,N-di-n-propyl(meth)acrylamide, N-isopropyl (meth)acrylamide, N,N-di-n-butyl(meth)acrylamide, N,N-di-n-hexyl(meth)acrylamide, N,N-di-n-octyl(meth)acrylamide, N,N-di-2-ethylhexyl(meth)acrylamide, N-(2-hydroxyethyl)(meth)acrylamide, N,N-bis(2-hydroxyethyl)(meth)acrylamide, N-acryloylmorpholine, N,N-dimethylaminoethyl(meth)acrylamide, N,N-diethylaminoethyl(meth)acrylamide, N,N-dipropylaminoethyl(meth)acrylamide, N,N-dibutylaminoethyl(meth)acrylamide, N,N-dimethylaminopropyl(meth)acrylamide, N,N-diethylaminopropyl(meth)acrylamide, N,N-dipropylaminopropyl(meth)acrylamide, N,N-dibutylaminopropyl(meth)acrylamide, N,N-dimethylaminobutyl(meth)acrylamide, N,N-diethylaminobutyl(meth)acrylamide, N,N-dipropylaminobutyl(meth)acrylamide, and N,N-dibutylaminobutyl(meth)acrylamide. These may be used alone, or two or more thereof may be used in combination. In view of improving the curability of the photocurable resin composition and the fracture resistance of the cured product, the (meth)acrylamide compound (D) is more preferably N,N-dimethyl(meth)acrylamide, N,N-diethyl(meth)acrylamide, N,N-di-n-propyl(meth)acrylamide, N-isopropyl (meth)acrylamide, N,N-di-n-butyl(meth)acrylamide, N-(2-hydroxyethyl)(meth)acrylamide, N-acryloylmorpholine, N,N-dimethylaminoethyl(meth)acrylamide, N,N-diethylaminoethyl(meth)acrylamide, N,N-dimethylaminopropyl (meth)acrylamide, N,N-diethylaminopropyl(meth)acrylamide, N,N-dimethylaminobutyl(meth)acrylamide, or N,N-diethylaminobutyl(meth)acrylamide, even more preferably N,N-dimethyl(meth)acrylamide, N,N-diethyl(meth)acrylamide, N-(2-hydroxyethyl)(meth)acrylamide, N-acryloylmorpholine, N,N-dimethylaminoethyl(meth)acrylamide, N,N-diethylaminoethyl(meth)acrylamide, N,N-dimethylaminopropyl(meth)acrylamide, or N,N-diethylaminopropyl(meth)acrylamide, particularly preferably N,N-dimethylacrylamide, N,N-diethylacrylamide, N-isopropylacrylamide, N-(2-hydroxyethyl)acrylamide, N-acryloylmorpholine, N,N-dimethylaminoethylacrylamide, N,N-diethylaminoethylacrylamide, N,N-dimethylaminopropylacrylamide, or N,N-diethylaminopropylacrylamide, most preferably N,N-diethylacrylamide or N,N-dimethylaminopropylacrylamide.

The content of (meth)acrylamide compound (D) in the photocurable resin composition of the present invention is preferably 1 to 70 mass %, more preferably 5 to 60 mass %, even more preferably 10 to 50 mass % relative to the total amount of urethanized (meth)acrylic compound (A), mono (meth)acrylic acid ester compound (B) containing no urethane bond, and (meth)acrylamide compound (D).

The photocurable resin composition of the present invention may comprise a polymerization accelerator (E) to improve photocurability, provided that addition of a polymerization accelerator is not detrimental to the gist of the present invention. Examples of the polymerization accelerator (E) include ethyl 4-(N,N-dimethylamino) benzoate, methyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino) benzophenone, and butyl 4-(N,N-dimethylamino)benzoate. The polymerization accelerator (E) may be used alone, or two or more thereof may be used in combination. In view of imparting desirable curability to the photocurable resin composition, the polymerization accelerator (E) is preferably at least one selected from the group consisting of ethyl 4-(N,N-dimethylamino)benzoate, n-butoxyethyl 4-(N,N-dimethylamino)benzoate, and 4-(N,N-dimethylamino)benzophenone.

The photocurable resin composition of the present invention may further comprise a filler (F), in order to adjust the paste characteristics, or to improve the mechanical strength of the cured product of the photocurable resin composition. Examples of the filler (F) include organic fillers, inorganic fillers, and organic-inorganic composite fillers. The filler (F) may be used alone, or two or more thereof may be used in combination.

Examples of the materials of the organic fillers include polymethyl methacrylate, polyethyl methacrylate, a methyl methacrylate-ethyl methacrylate copolymer, crosslinked polymethyl methacrylate, crosslinked polyethyl methacrylate, polyesters, polyamides, polycarbonates, polyphenylene ethers, polyoxymethylene, polyvinyl chloride, polystyrene, polyethylene, polypropylene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used in combination. The organic filler is not limited to a particular shape, and may be appropriately selected from organic fillers of different particle diameters.

Examples of the materials of the inorganic fillers include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in combination. The inorganic filler is not limited to a particular shape, and may be appropriately selected from inorganic fillers of different shapes, such as irregular fillers, and spherical fillers.

The photocurable resin composition of the present invention may comprise a polymer to alter properties such as flexibility and flowability, provided that the addition of a polymer is not detrimental to the gist of the present invention. Examples of the polymer that may be added in the present invention include natural rubber, synthetic polyisoprene rubber, liquid polyisoprene rubber, hydrogenated products of these, polybutadiene rubber, liquid polybutadiene rubber, hydrogenated products of these, styrene-butadiene rubber, chloroprene rubber, ethylene-propylene rubber, acryl rubber, isoprene-isobutylene rubber, acrylonitrile-butadiene rubber, and styrene elastomers. Specific examples of other polymers that may be added in the present invention include a polystyrene-polyisoprene-polystyrene block copolymer, a polystyrene-polybutadiene-polystyrene block copolymer, a poly(α-methylstyrene)-polybutadiene-poly(α-methylstyrene) block copolymer, a poly(p-methylstyrene)-polybutadiene-poly(p-methylstyrene) block copolymer, and hydrogenated products of these. These may be used alone, or two or more thereof may be used in combination.

The photocurable resin composition of the present invention may optionally comprise a softener. Examples of the softener include petroleum-base softeners such as paraffinic, naphthenic, and aromatic process oils, and vegetable oil-base softeners such as paraffin, peanut oil, and rosin. These softeners may be used alone, or two or more thereof may be used in combination. The softener content is not particularly limited, provided that it is not detrimental to the gist of the present invention. Typically, the softener content is at most 200 parts by mass, preferably at most 100 parts by mass relative to total 100 parts by mass of urethanized (meth)acrylic compound (A), mono(meth)acrylic acid ester compound (B) containing no urethane bond, and (meth)acrylamide compound (D).

The photocurable resin composition of the present invention may comprise a known stabilizer, in order to inhibit deterioration, or to adjust photocurability. Examples of such stabilizers include polymerization inhibitors, ultraviolet absorbers, and antioxidants.

Examples of the polymerization inhibitors include hydroquinone, hydroquinone monomethyl ether, dibutylhydroquinone, dibutylhydroquinone monomethyl ether, 4-t-butyl catechol, 2-t-butyl-4,6-dimethylphenol, 2,6-di-t-butylphenol, and 3,5-di-t-butyl-4-hydroxytoluene. The content of the polymerization inhibitor is preferably 0.001 to 1.0 parts by mass relative to total 100 parts by mass of urethanized (meth)acrylic compound (A), mono(meth)acrylic acid ester compound (B) containing no urethane bond, and (meth)acrylamide compound (D).

The photocurable resin composition of the present invention may comprise a known additive, in order to adjust shades or paste characteristics. Examples of such additives include pigments, dyes, organic solvents, and thickeners.

The photocurable resin composition of the present invention has good fabricability, and exhibits superior flexibility, shock absorption, fracture resistance, and water resistance in the form of a cured product. The photocurable resin composition of the present invention is therefore usable in applications where such advantages can be exploited, most suitably as a mouthguard, an occlusal splint, or a denture base material. A cured product using the photocurable resin composition of the present invention may have a shape that depends on intended use. In the photocurable resin composition of the present invention, the type and content of each component (urethanized (meth)acrylic compound (A), mono(meth)acrylic acid ester compound (B) containing no urethane bond, photopolymerization initiator (C), (meth)acrylamide compound (D), and optional components such as polymerization accelerator (E), filler (F), a polymer, a softener, a stabilizer, and an additive) may be optionally adjusted according to use (for example, a mouthguard, an occlusal splint, or a denture base material).

The photocurable resin composition of the present invention can be used in a wide variety of applications by taking advantage of its characteristics, specifically, the superior dimensional accuracy due to the low rate of volume shrinkage upon curing with light, and the ability to produce cured products of desirable characteristics, for example, molded products or three-dimensional objects having desirable flexibility and desirable mechanical characteristics. For example, the photocurable resin composition of the present invention can be used for the stereolithographic production of a three-dimensional object, the production of various molded products, for example, a film-shaped object or a molding produced by a technique such as flow casting or casting, and a the for coating or vacuum molding.

The photocurable resin composition of the present invention is particularly suited for stereolithography. In stereolithography applications, the photocurable resin composition of the present invention enables smooth production of a three-dimensional object having desirable flexibility and mechanical characteristics while ensuring superior dimensional accuracy with a maintained low rate of volume shrinkage at the time of curing with light.

Another embodiment of the present invention is a method for producing a three-dimensional object by stereolithography using any of the photocurable resin compositions described above.

In stereolithography using a photocurable resin composition of the present invention, any known stereolithography method and device may be used (for example, a stereolithography device such as the DigitalWax® 028J-Plus manufactured by DWS). In the present invention, the light energy used to cure the resin is preferably an active energy beam. As used herein, "active energy beam" means an energy ray capable of curing a light-curable resin composition, and includes, for example, ultraviolet light, an electron beam, X-rays, radiant rays, and high-frequency waves. For example, the active energy beam may be ultraviolet light of 300 to 400 nm wavelengths. The light source of active energy beam may be, for example, a laser such as an Ar laser or a He—Cd laser; or a lighting such as a halogen lamp, a xenon lamp, a metal halide lamp, an LED, a mercury lamp, and a fluorescent lamp. Lasers are particularly preferred. When the light source is a laser, the fabrication time can be reduced by increasing the energy level, and a three-dimensional object of high shape precision can be obtained by taking advantage of the desirable convergence of a laser beam.

Stereolithography using a photocurable resin composition of the present invention may use any known method and any known stereolithography system, and the method and device are not particularly limited, as mentioned above. However, a typical example of a stereolithography method preferred for use in the present invention is a method that produces a three-dimensional object of the desired shape through a repeated procedure that includes a step of forming a cured layer by selectively applying an active energy beam to the photocurable resin composition to obtain a cured layer having a desired pattern, and a step of continuously forming another cured layer by similarly applying an active energy beam to a newly supplied, uncured liquid photocurable resin composition. The resulting three-dimensional object may be used as it is, or may be used after improving mechanical characteristics, shape stability, or other properties by, for example, post-curing the product under applied light or heat.

The three-dimensional object obtained by stereolithography is not limited to a particular structure, shape, or size, and these may be decided according to use. Typical examples of areas to which the stereolithography of the present invention is applicable include production of various models and molds, including, for example, models for assessing external designs in a designing process; models for checking functions of components and parts; resin molds for making molds; base models for making dies; and direct molds for prototype dies. More specifically, the stereolithography of the present invention is applicable to, for example, production of models or work models for precision components and parts, electrical and electronic components, furniture, architectural structures, automobile parts, various containers and vessels, castings, dies, and base molds. Particularly, by taking advantage of the desirable flexibility and elastic recovery of the photocurable resin composition, the present invention can be used very effectively for cushioning materials of complex shapes used in structures (for example, architectural structures), and for dies for vacuum molding.

EXAMPLES

The following describes the present invention in greater detail by way of Examples. It should be noted, however, that the present invention is in no way limited by the following Examples, and various changes may be made by a person with ordinary skill in the art within the technical idea of the present invention.

Synthesis Example 1

Production of Urethanized (Meth)Acrylic Compound (A-1)

(1) First, 250 g of isophorone diisocyanate, and 0.15 g of di-n-butyltin dilaurate were added into a 5 L four-neck flask equipped with a stirrer, a thermostat, a thermometer, and a condenser, and the mixture was heated to 70° C. while being stirred.

(2) Separately, 2,500 g of a polyester polyol (Kuraray Polyol® P-5010 manufactured by Kuraray Co., Ltd.; a polymer of adipic acid and 3-methyl-1,5-pentanediol, a weight-average molecular weight Mw of 5,000) was added into a dropping funnel equipped with a side tube, and the solution in the dropping funnel was dropped into the flask of (1). Here, the solution was chopped at a constant rate over a time period of 4 hours with the temperature inside the flask held at 65 to 75° C. while stirring the solution in the flask of (1). After dropping, the mixture was stirred at the same temperature for 2 hours to allow for reaction.

(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound (A-1).

Synthesis Example 2

Production of Urethanized (Meth)Acrylic Compound (A-2)

(1) First, 250 g of isophorone diisocyanate, and 0.15 g of di-n-butyltin dilaurate were added into a 5 L four-neck flask equipped with a stirrer, a thermostat, a thermometer, and a condenser, and the mixture was heated to 70° C. while being stirred.

(2) Separately, 500 g of a polycarbonate polyol (Kuraray Polyol® C-1090 manufactured by Kuraray Co., Ltd.; a polymer of 1,6-hexanediol/3-methyl-1,5-pentanediol=9/1 (mass ratio), a weight-average molecular weight Mw of 1,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow for reaction.

(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound (A-2).

Synthesis Example 3

Production of Urethanized (Meth)Acrylic Compound (A-3)

(1) First, 195 g of 2,4-tolylene diisocyanate, and 0.15 g of cli-n-butyltin dilaurate were added into a 5 L four-neck flask equipped with a stirrer, a thermostat, a thermometer, and a condenser, and the mixture was heated to 70° C. while being stirred.

(2) Separately, 1,250 g of a polybutylene glycol (Uniol® PB-1000 manufactured by NOF Corporation, a weight-average molecular weight Mw of 1,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow for reaction.

(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a urethanized (meth)acrylic compound (A-3).

Synthesis Example 4

Production of Urethanized (Meth)Acrylic Compound (A-4)

First, 390 g of isophorone diisocyanate, 3.5 g of aluminum chelate M (aluminum alkylacetoacetate diisopropylate), and 200 g of 2-hydroxyethyl acrylate were mixed in a 5 L SUS autoclave in an air atmosphere, and the mixture was allowed to react at 60° C. for 1 hour to synthesize a reaction product A. After synthesis, 600 g of the synthesized reaction product A, 1,500 g of hydrogenated polybutadiene hydroxy-modified at the both ends (GI-1000 manufactured by Nippon Soda Co., Ltd., a number average molecular weight Mn of 1,500, Mw/Mn=1.15, a 1,2-linkage unit content of 7 mol % (a fraction of the number of moles of 1,2-linkage unit with respect to the total number of moles of 1,2-linkage unit and 1,4-linkage unit), a hydrogenation rate of 96 mol % as measured by iodine value), and 12.0 g of aluminum chelate M were mixed in an air atmosphere, and the mixture was allowed to react at 60° C. for 2 hours. After dilution with 1 L of toluene, the reaction mixture was washed with 0.5 L of distilled water three times, and reprecipitated with a 50:50 solvent of distilled water and methanol (volume ratio), followed by drying under reduced pressure to obtain a urethanized (meth)acrylic compound (A-4).

The components used for the photocurable resin compositions of Examples and Comparative Example are listed below with the abbreviations used.

Mono(Meth)Acrylic Acid Ester Compound (B) Containing No Urethane Bond

POBA: m-Phenoxybenzyl acrylate (manufactured by Kyoeisha Chemical Co., Ltd.)

EPPA: Ethoxylated-o-phenylphenol acrylate (manufactured by Shin-Nakamura Chemical Co., Ltd.)

Photopolymerization Initiator (C)

TPO: 2,4,6-Trimethylbenzoyldiphenylphosphine oxide

BAPO: Bis(2,4,6-trimethylbenzoyl)phenylphosphine oxide (Meth)Acrylamide Compound (D)

DEAA: N,N-Diethylacrylamide (manufactured by KJ Chemicals Corporation)

ACMO: N-Acryloylmorpholine (manufactured by KJ Chemicals Corporation)

Polymerization Inhibitor

BHT: 3,5-di-t-Butyl-4-hydroxytoluene

Examples 1 to 7 and Comparative Examples 1 to 4

The components were mixed under ordinary temperature (20° C.±15° C., JIS (Japanese Industrial Standards) Z 8703: 1983) in the amounts shown in Tables 1 and 2 to prepare pastes as photocurable resin compositions of Examples 1 to 7 and Comparative Examples 1 to 4.

Fabricability

The photocurable resin compositions of Examples and Comparative Examples were each fabricated into a sheet measuring 2 mm in thickness, 11 cm in length, and 5 cm in width, using a stereolithography device (DigitalWax® 028J-Plus, manufactured by DWS). The photocurable resin composition was determined as "Satisfactory" when it was fabricable into a sheet of the desired dimensions, and "Unsatisfactory" when the photocurable resin composition was not fabricable into the desired object. The sheets were used for the following evaluations.

Flexibility (Hardness)

For the cured product of each photocurable resin composition according to Examples and Comparative Examples, a 4 mm-thick specimen was prepared by stacking two sheets of the photocurable resin composition. The specimen was used to measure the hardness (A hardness) of the cured product at 23° C. according to JIS K 7215:1986, using a type A durometer (Asker Rubber Hardness Meter, Type A, Model Number 32330, manufactured by Kobunshi Keiki Co., Ltd.). The hardness was measured as an index of flexibility. The results are presented in Tables 1 and 2. In the measurement, the cured product can be said as having desirable flexibility when the A hardness at 23° C. is 70 to 85.

Shock Absorption (Coefficient of Restitution)

Shock absorption was measured by drop impact test. For the cured product of each photocurable resin composition according to Examples and Comparative Examples, two sheets of the cured product, 4 mm thick together, were put on top of each other on a stone table, and a steel ball (0=⅜ inches; 3.58 g) was dropped in free fall from a height of 50 cm. The height of the bounce was then measured for calculation of a coefficient of restitution. The coefficient of restitution was calculated using the following formula. Shock absorption is desirable when the coefficient of restitution is 30 or less.

$$\text{Coefficient of restitution} = [\text{bounce height (cm)}/50 \text{ (cm)}] \times 100$$

Fracture Resistance (Tear Strength)

For the cured product of each photocurable resin composition according to Examples and Comparative Examples, the sheet was prepared into a specimen having the same dimensions as the trouser-shaped specimen of JIS K 6252-1:2015 (Rubber, Vulcanized or Thermoplastic-Determination of Tear Strength), using a punching blade. The specimen was used in a tensile test conducted at a test speed of 500 mm/min. Fracture resistance is desirable when the measured tear strength is 20 kN/m or more.

Fracture Resistance (Tensile Strength and Tensile Elongation)

For the cured product of each photocurable resin composition according to Examples and Comparative Examples, the sheet was prepared into a specimen having the same dimensions as the dumbbell-shaped specimen 8 of JIS K 6251:2010 (Rubber, Vulcanized or Thermoplastics-Determination of Tensile Stress-Strain Properties), using a punching blade. The specimen was used in a tensile test conducted at a test speed of 500 mm/min. Fracture resistance is desirable when the measured tensile strength is 5.0 MPa or more and the measured tensile elongation (elongation at break) is 50% or more.

Water Resistance

The cured products of the photocurable resin compositions according to Examples and Comparative Examples were measured for tear strength and tensile strength as above after being immersed in 37° C. water for 24 hours. Water resistance is desirable when the rate of change (rate of decrease) of tear strength and tensile strength after 24-hour immersion in 37° C. water is 10% or less relative to the initial tear strength and tensile strength.

Rate of change of tear strength (%)=[{initial tear strength (kN/m)−tear strength after immersion in water (kN/m)}/initial tear strength (kN/m)]× 100

Rate of change of tensile strength (%)=[{initial tensile strength (MPa)−tensile strength after immersion in water (MPa)}/initial tensile strength (MPa)]×100

TABLE 1

|  |  |  | Examples |  |  |  |  |  |  |
| --- | --- | --- | --- | --- | --- | --- | --- | --- | --- |
|  |  |  | 1 | 2 | 3 | 4 | 5 | 6 | 7 |
| Raw materials (parts by mass) | Urethanized (meth)acrylic compound (A-1) | | 40 | | | | | | |
|  | Urethanized (meth)acrylic compound (A-2) | | | 60 | 60 | 40 | 50 | | |
|  | Urethanized (meth)acrylic compound (A-3) | | | | | | | 60 | |
|  | Urethanized (meth)acrylic compound (A-4) | | | | | | | | 40 |
|  | POBA | | 60 | 40 | | 40 | 40 | 40 | 40 |
|  | EPPA | | | | 40 | | | | |
|  | DEAA | | | | | 20 | | | 10 |
|  | ACMO | | | | | | 10 | | 10 |
|  | TPO | | 2.0 | 2.0 | 2.0 | 2.0 | 2.0 | 2.0 | 3.0 |
|  | BAPO | | 0.5 | | | | | | 0.5 |
|  | BHT | | 0.05 | 0.05 | 0.05 | 0.05 | 0.05 | 0.05 | 0.05 |
| Properties | Fabricability | | Satis-factory | Satis-factory | Satis-factory | Satis-factory | Satis-factory | Satis-factory | Satis-factory |
|  | Flexibility | Hardness | 75 | 80 | 81 | 82 | 83 | 78 | 72 |
|  | Shock absorption | Coefficient of restitution | 18 | 20 | 22 | 24 | 25 | 21 | 15 |
|  | Fracture resistance | Tear strength (kN/m) | 22 | 25 | 24 | 26 | 27 | 24 | 21 |
|  |  | Tensile strength (MPa) | 12 | 15 | 14 | 17 | 18 | 13 | 12 |
|  |  | Tensile elongation (%) | 100 | 80 | 90 | 70 | 60 | 70 | 120 |
|  | Water resistance | Tear strength after immersion (kN/m) | 22 | 24 | 23 | 24 | 25 | 23 | 20 |
|  |  | Rate of change (%) | 0 | 4.0 | 4.2 | 7.7 | 7.4 | 4.2 | 4.8 |
|  |  | Tensile strength after immersion (MPa) | 12 | 14 | 13 | 16 | 17 | 12 | 11 |
|  |  | Rate of change (%) | 0 | 6.7 | 7.1 | 5.9 | 5.6 | 7.7 | 8.3 |

TABLE 2

|  |  |  | Comparative Examples |  |  |  |
| --- | --- | --- | --- | --- | --- | --- |
|  |  |  | 1 | 2 | 3 | 4 |
| Raw materials (parts by mass) | Urethanized (meth)acrylic compound (A-2) | | 60 | 60 | 60 | 60 |
|  | ACMO[1] | | 40 | | | |
|  | IBA[2] | | | 40 | | |
|  | BA[3] | | | | 40 | |
|  | PEA[4] | | | | | 40 |
|  | TPO | | 2.0 | 2.0 | 2.0 | 2.0 |
|  | BHT | | 0.05 | 0.05 | 0.05 | 0.05 |
| Properties | Fabricability | | Satis-factory | Satis-factory | Unsatis-factory | Unsatis-factory |
|  | Flexibility | Hardness | 95 | 92 | | |
|  | Shock absorption | Coefficient of restitution | 58 | 52 | | |
|  | Fracture resistance | Tear strength (kN/m) | 32 | 28 | | |
|  |  | Tensile strength (MPa) | 18 | 16 | | |
|  |  | Tensile elongation (%) | 30 | 40 | | |
|  | Water resistance | Tear strength after immersion (kN/m) | 27 | 24 | | |
|  |  | Rate of change (%) | 16 | 14 | | |
|  |  | Tensile strength after immersion (MPa) | 14 | 12 | | |
|  |  | Rate of change (%) | 22 | 25 | | |

[1] ACMO: N-Acryloylmorpholine (NK Ester A-MO manufactured by Shin-Nakamura Chemical Co., Ltd.
[2] IBA: Isobornyl acrylate (manufactured by Wako Pure Chemical Corporation)
[3] BA: Benzyl acrylate (Light Ester BZ manufactured by Kyoeisha Chemical Co., Ltd.)
[4] PEA: Phenoxyethyl acrylate (Light Ester PO manufactured by Kyoeisha Chemical Co., Ltd.)

As shown in Tables 1 and 2, the cured products of the photocurable resin compositions of Examples 1 to 7 had good fabricability, and were also superior in terms of flexibility, shock absorption, fracture resistance, and water resistance. Specifically, the cured products of the photocurable resin compositions according to Examples 1 to 7 had more desirable flexibility than the cured products of the photocurable resin compositions according to Comparative Examples 1 and 2. The cured products of the photocurable resin compositions according to Examples 1 to 7 had more desirable shock absorption than the cured products of the photocurable resin compositions according to Comparative Examples 1 and 2. The cured products of the photocurable resin compositions according to Examples 1 to 7 had more desirable fracture resistance than the cured products of the photocurable resin compositions according to Comparative Examples 1 and 2. The cured products of the photocurable resin compositions according to Examples 1 to 7 had more desirable water resistance than the cured products of the photocurable resin compositions according to Comparative Examples 1 and 2. The photocurable resin compositions according to Examples 1 to 7 had more desirable fabricability than the photocurable resin compositions according to Comparative Examples 3 and 4. The photocurable resin compositions according to Comparative Examples 3 and 4 were not fabricable into sheets, and did not allow measurements of various properties.

INDUSTRIAL APPLICABILITY

A photocurable resin composition of the present invention has good fabricability, and exhibits superior flexibility, shock absorption, fracture resistance, and water resistance in the form of a cured product. This makes a photocurable resin composition of the present invention particularly suited for mouthguards, occlusal splints, and denture base materials.

The invention claimed is:

1. A photocurable resin composition, comprising:
a urethanized (meth)acrylic compound (A);
a mono(meth)acrylic acid ester compound (B) comprising no urethane bond; and
a photopolymerization initiator (C),
wherein the urethanized (meth)acrylic compound (A) is a (meth)acrylate comprising, per molecule, at least one structure selected from the group consisting of a polyester, a polycarbonate, a polyurethane, a polyether, a poly-conjugated diene, and a hydrogenated poly-conjugated diene, and a urethane bond,
the mono(meth)acrylic acid ester compound (B) comprises at least one selected from the group consisting of a mono(meth)acrylic acid ester compound (b-I) of formula (I):

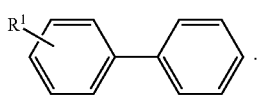

and a mono(meth)acrylic acid ester compound (b-II) of formula (II):

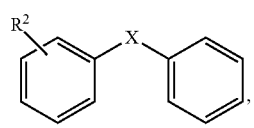

X being O or a divalent hydrocarbon group comprising 1 to 6 carbon atoms, and $R^1$ and $R^2$ each independently being a group of formula (i)

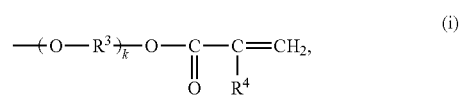

or
a group of formula (ii)

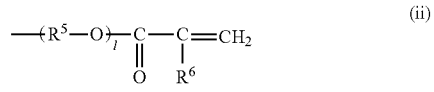

wherein
$R^3$ and $R^5$ are each independently a divalent hydrocarbon group having 1 to 10 carbon atoms,
$R^4$ and $R^6$ are each independently H or a methyl group
k is an integer in a range of from 1 to 6, and
l is independently an integer in a range of from 0 to 6.

2. The composition of claim 1, further comprising:
a (meth)acrylamide compound (D).

3. The composition of claim 1, wherein $R^4$ and $R^6$ are H.

4. The composition of claim 1, wherein the group of formula (i) is present and k is 1.

5. The composition of claim 1, wherein the mono(meth)acrylic acid ester compound (B) comprises the mono(meth)acrylic acid ester compound (b-II), and X is O.

6. The composition of claim 5, wherein $R^2$ is the group of formula (ii).

7. The composition of claim 1, wherein the mono(meth)acrylic acid ester compound (B) comprises the mono(meth)acrylic acid ester compound (b-I), and $R^1$ is the group of formula (i).

8. The composition of claim 1, wherein the photocurable resin composition is suitable for stereolithography.

9. A mouthguard, comprising:
a cured product of the photocurable resin composition of claim 1.

10. An occlusal splint, comprising:
a cured product of the photocurable resin composition of claim 1.

11. A denture base material, comprising:
a cured product of the photocurable resin composition of claim 1.

12. A method, comprising:
stereolithographically producing a three-dimensional object with the photocurable resin composition of claim 1.

13. The composition of claim 1, having, in cured dumbbell form with dimensions of specimen 8 of JIS K 6251:2010 (Rubber, Vulcanized or Thermoplastics Determination of Tensile Stress-Strain Properties), using a punching blade at a test speed of 500 mm/min, a tensile elongation of 50% or more.

14. The composition of claim 13, wherein the tensile elongation is in a range of from 60 to 120%.

15. The composition of claim 1, having, in cured form, an A hardness at 23° C. is in a range of from 70 to 85.

16. The composition of claim 1, having, in cured dumbbell form with dimensions of specimen 8 of JIS K 6251:2010 (Rubber, Vulcanized or Thermoplastics Determination of Tensile Stress-Strain Properties), using a punching blade at a test speed of 500 mm/min, a tensile strength of 5.0 MPa or more.

17. The composition of claim 16, wherein the tensile strength is in a range of from 12 to 18 MPa.

18. The composition of claim 1, having, in cured form, a coefficient of restitution of 30 or less, wherein the coefficient of restitution is determined based on two sheets of cured product, 4 mm thick together, being put on top of each other on a stone table, and a 3.58 g steel ball of ⅜ inch diameter being dropped in free fall from a height of 50 cm, and measuring a height of a bounce for calculating the coefficient of restitution with a formula coefficient of restitution=[bounce height (cm)/50 (cm)]×100.

19. The composition of claim 18, wherein the coefficient of restitution is in a range of from 15 to 25.

20. The composition of claim 1, wherein the group of formula (ii) is present and 1 is 0 or 1.

* * * * *